United States Patent [19]
Kurnit et al.

[11] Patent Number: 6,033,854
[45] Date of Patent: Mar. 7, 2000

[54] QUANTITATIVE PCR USING BLOCKING OLIGONUCLEOTIDES

[75] Inventors: David M. Kurnit, Ann Arbor; Pei-Wen Chiang, Farmington, both of Mich.; Chang-Ning J. Wang, Chelmsford, Mass.

[73] Assignee: Biotronics Corporation, Lowell, Mass.

[21] Appl. No.: 09/014,065

[22] Filed: Jan. 27, 1998

Related U.S. Application Data

[60] Continuation-in-part of application No. 08/434,474, May 4, 1995, Pat. No. 5,712,386, which is a division of application No. 08/250,849, May 26, 1994, Pat. No. 5,567,583, which is a continuation-in-part of application No. 07/808,463, Dec. 16, 1991, Pat. No. 5,348,853.

[51] Int. Cl.[7] .............. C12Q 1/68; C12P 19/34; C07H 21/04
[52] U.S. Cl. .................. 435/6; 435/91.2; 536/24.3; 536/24.33
[58] Field of Search .................. 435/6, 91.2, 810; 536/24.3, 24.33

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,683,202 | 7/1987 | Mullis | 435/91 |
| 4,725,537 | 2/1988 | Fritsch et al. | 435/6 |
| 4,800,159 | 1/1989 | Mullis et al. | 435/172.3 |
| 4,822,733 | 4/1989 | Morrison | 435/6 |
| 4,965,188 | 10/1990 | Mullis et al. | 435/6 |
| 4,996,143 | 2/1991 | Heller et al. | 435/6 |
| 5,038,852 | 8/1991 | Johnson et al. | 165/12 |
| 5,210,015 | 5/1993 | Gelfand et al. | 435/6 |
| 5,348,853 | 9/1994 | Wang et al. | 435/6 |
| 5,567,583 | 10/1996 | Wang et al. | 435/6 |

FOREIGN PATENT DOCUMENTS

| | | |
|---|---|---|
| 0 200 362 A2 | 12/1986 | European Pat. Off. . |
| 0 201 184 A2 | 12/1986 | European Pat. Off. . |
| 0 236 069 | 9/1987 | European Pat. Off. . |
| 0 320 308 | 6/1989 | European Pat. Off. . |
| 0 333 465 | 9/1989 | European Pat. Off. . |
| 0 382 433 A2 | 8/1990 | European Pat. Off. . |
| WO 89/09835 | 10/1989 | WIPO . |

OTHER PUBLICATIONS

Cairns et al., Clin. Cancer Res. 4(2), 441–444, 1998.
Chiang et al., Cytog. Cell Genet. 79(1–2), 50, 1997.
Blanco et al., "Highly Effecient DNA Synthesis by the Phage Ø29 DNA Polymerase," *J. Biol. Chem.*, 264:8935–8940, 1989.
Holland et al., "Doctrine of Specific–polymerace Chain Reaction Product . . . ", *Proc. Natl. Sci. Acad. USA*, 88:7276–7280, 1991.
Morrison et al., "Solution–phase Detection of Polynucleotides Using Interacting Fluorescent Labels and Competitive Hybridization," *Analytical Biochemistry*, 183:231–244, 1989.
Walker et al., "Isothermal In Vitro Amplification of DNA by a Restriction Enzyme/DNA Polymerase System", *Proc. Natl. Acad. Sci. USA*, 89:392–390, 1996.
Augenlicht et al., "Low–Level c–myc Amplification in Human Colonic Carcinoma Cell Lines and Tumors: A Frequent , p53–independent Mutation Associated with Improved Outcome in a Randomized Multi–institutional Trial," *Cancer Research*, 57:1769–1775, 1997.
Chiang et al., "Use of a Fluorescent–PCR Reaction to Detect Genomic Sequence Copy Number and Transcriptional Abundance," *Genome Research,* 6:1013–1026, 1996.
Gibson et al., "A Novel Method for Real Time Quantitative RT–PCR," *Genome Research,* 6:995–1001, 1996.
Heid et al., "Real Time Quantitative PCR," *Genome Research,* 6:986–994, 1996.
von Eggeling et al., "Rapid Detection of Trisomy 21 by Quantitative PCR," *Human Genetics,* 91:567–570, 1993.

*Primary Examiner*—Kenneth R. Horlick
*Attorney, Agent, or Firm*—Fish & Richardson P.C.

[57] ABSTRACT

Disclosed is a method for determining the number of copies of a target nucleic acid relative to the number of copies of a reference nucleic acid in a biological specimen. The method includes amplifying the target nucleic acid, measuring the amplification of the target nucleic acid, amplifying the reference nucleic acid, measuring the amplification of the target nucleic acid, and comparing the amplification of the target nucleic acid sequence to the amplification of the reference nucleic acid sequence.

23 Claims, No Drawings

SEQUENCE LISTING

```
<160> NUMBER OF SEQ ID NOS: 24

<210> SEQ ID NO 1
<211> LENGTH: 20
<212> TYPE: DNA
<213> ORGANISM: Homo sapiens

<400> SEQUENCE: 1
cccagagtca gctcgtgttg                                              20

<210> SEQ ID NO 2
<211> LENGTH: 24
<212> TYPE: DNA
<213> ORGANISM: Homo sapiens

<400> SEQUENCE: 2
gggtcaggcc agacaccacc atgg                                         24

<210> SEQ ID NO 3
<211> LENGTH: 23
<212> TYPE: DNA
<213> ORGANISM: Homo sapiens

<400> SEQUENCE: 3
aattgacagc ttcaacagaa agg                                          23

<210> SEQ ID NO 4
<211> LENGTH: 18
<212> TYPE: DNA
<213> ORGANISM: Homo sapiens

<400> SEQUENCE: 4
aaggtggcag ctgagtgg                                                18

<210> SEQ ID NO 5
<211> LENGTH: 18
<212> TYPE: DNA
<213> ORGANISM: Homo sapiens

<400> SEQUENCE: 5
ctgagtctga attggagg                                                18

<210> SEQ ID NO 6
<211> LENGTH: 20
<212> TYPE: DNA
<213> ORGANISM: Homo sapiens
```

-continued

```
<400> SEQUENCE: 6
ctgcttattt cttgttctgg                                               20

<210> SEQ ID NO 7
<211> LENGTH: 20
<212> TYPE: DNA
<213> ORGANISM: Homo sapiens

<400> SEQUENCE: 7
actgaaagcc ttagggaagc                                               20

<210> SEQ ID NO 8
<211> LENGTH: 22
<212> TYPE: DNA
<213> ORGANISM: Homo sapiens

<400> SEQUENCE: 8
aagcactctg tacaaagcct gg                                            22

<210> SEQ ID NO 9
<211> LENGTH: 24
<212> TYPE: DNA
<213> ORGANISM: Homo sapiens

<400> SEQUENCE: 9
tactgccccc catgaggaag gaac                                          24

<210> SEQ ID NO 10
<211> LENGTH: 21
<212> TYPE: DNA
<213> ORGANISM: Homo sapiens

<400> SEQUENCE: 10
gatgaggcaa agactatgcc g                                             21

<210> SEQ ID NO 11
<211> LENGTH: 25
<212> TYPE: DNA
<213> ORGANISM: Homo sapiens

<400> SEQUENCE: 11
cccaggtacc cttctcccag agtgg                                         25

<210> SEQ ID NO 12
<211> LENGTH: 22
<212> TYPE: DNA
<213> ORGANISM: Homo sapiens

<400> SEQUENCE: 12
tactaggctg cctgtcactg tc                                            22

<210> SEQ ID NO 13
<211> LENGTH: 21
<212> TYPE: DNA
<213> ORGANISM: Homo sapiens

<400> SEQUENCE: 13
cttttcaccc atctacagtc c                                             21

<210> SEQ ID NO 14
<211> LENGTH: 23
<212> TYPE: DNA
<213> ORGANISM: Homo sapiens
```

<400> SEQUENCE: 14
ggccaggcat tgaagtctca tgg                                    23

<210> SEQ ID NO 15
<211> LENGTH: 24
<212> TYPE: DNA
<213> ORGANISM: Homo sapiens

<400> SEQUENCE: 15
tctgtgactt gcacggtcag ttgc                                   24

<210> SEQ ID NO 16
<211> LENGTH: 21
<212> TYPE: DNA
<213> ORGANISM: Homo sapiens

<400> SEQUENCE: 16
agacctccag catccaggtg g                                      21

<210> SEQ ID NO 17
<211> LENGTH: 25
<212> TYPE: DNA
<213> ORGANISM: Homo sapiens
<220> FEATURE:
<221> NAME/KEY: misc_feature
<222> LOCATION: (1)...(25)
<223> OTHER INFORMATION: n = A,T,C or G

<400> SEQUENCE: 17
gcatcggggt angcgcggcg gatgg                                  25

<210> SEQ ID NO 18
<211> LENGTH: 22
<212> TYPE: DNA
<213> ORGANISM: Homo sapiens

<400> SEQUENCE: 18
ccactcctgt gctgcgaagt gg                                     22

<210> SEQ ID NO 19
<211> LENGTH: 20
<212> TYPE: DNA
<213> ORGANISM: Homo sapiens

<400> SEQUENCE: 19
tctgatgtgt cctactccac                                        20

<210> SEQ ID NO 20
<211> LENGTH: 20
<212> TYPE: DNA
<213> ORGANISM: Homo sapiens

<400> SEQUENCE: 20
gcaagtcata agggatttc                                         20

<210> SEQ ID NO 21
<211> LENGTH: 25
<212> TYPE: DNA
<213> ORGANISM: Homo sapiens

<400> SEQUENCE: 21
gttacaattg ctctcactcc actcc                                  25

-continued

```
<210> SEQ ID NO 22
<211> LENGTH: 23
<212> TYPE: DNA
<213> ORGANISM: Homo sapiens

<400> SEQUENCE: 22
agctggggaa tagagtgaga ttc                                        23

<210> SEQ ID NO 23
<211> LENGTH: 25
<212> TYPE: DNA
<213> ORGANISM: Homo sapiens

<400> SEQUENCE: 23
aaattgcatg tctctggggt acgga                                      25

<210> SEQ ID NO 24
<211> LENGTH: 25
<212> TYPE: DNA
<213> ORGANISM: Homo sapiens

<400> SEQUENCE: 24
agaaagaaag atagacagac aaacg                                      25
```

QUANTITATIVE PCR USING BLOCKING OLIGONUCLEOTIDES

CROSS REFERENCE TO RELATED APPLICATIONS

This application is a continuation-in-part of application Ser. No. 08/434,474, filed May 4, 1995, U.S. Pat. No. 5,712,386, which is a divisional application of application Ser. No. 08/250,849, filed May 26, 1994, now issued as U.S. Pat. No. 5,567,583, which is a continuation-in-part of application Ser. No. 07/808,463, filed Dec. 16, 1991, now issued as U.S. Pat. No. 5,348,853.

STATEMENT AS TO FEDERALLY SPONSORED RESEARCH

This research has been funded by grants from the National Institutes of Health. The federal government may have certain rights in this invention.

BACKGROUND OF THE INVENTION

The invention relates to a method for determining the copy number of a nucleic acid sequence.

Variation in the copy number of particular nucleic acid sequences, including amplification or deletion, underlies a variety of human disorders. In cancer, amplification of oncogenes or deletion of tumor suppressor genes is found frequently in primary tumors. Currently, detection of variations in the copy number of a particular DNA sequence can be accomplished by one of several methods, such as identifying deletions by loss of heterozygosity (LOH) analyses, and identifying amplifications by Southern blotting analyses.

LOH studies rely on informative sequence variations occurring near the particular DNA sequence of interest and can utilize either polymerase chain reaction (PCR) or Southern blot hybridization analysis to identify the loss of a genomic DNA sequence variant. LOH studies are consequently restricted by the need for polymorphic markers. Particular markers can be uninformative in a given case and can also be located some distance from the DNA sequence of interest.

Other methods, such as quantitative Southern blotting and fluorescence in situ hybridization can detect both deletions and amplifications of a target sequence without the heterozygosity requirements of RFLP or PCR typing methods. However, these methods offer limited resolution, can be technically difficult, labor-intensive, and may require large amounts of material or specialized tissue samples.

SUMMARY OF THE INVENTION

The invention features a method for quickly and sensitively determining the copy number of a target nucleic acid sequence relative to the copy number of a reference nucleic acid sequence in a small sample of a biological fluid.

One aspect of the invention relates to a method for determining the number of copies of a target nucleic acid relative to the number of copies of a reference nucleic acid in a biological specimen, which includes the steps of: (i) amplifying the target nucleic acid in the specimen with a polymerase, a first primer specific for the target nucleic acid with or without a segment noncontiguous to a first priming sequence, a second primer specific for the target nucleic acid with or without a segment noncontiguous to a second priming sequence in the presence of a first oligonucleotide which is incapable of acting as a primer for the polymerase, wherein the first oligonucleotide has at least 5 consecutive nucleotides fully complementary to at least 5 consecutive nucleotides of the first primer; (ii) measuring the amplification of the target nucleic acid; (iii) amplifying the reference nucleic acid in the specimen with a polymerase, a third primer specific for the reference nucleic acid with or without a segment noncontiguous to a third priming sequence, and a fourth primer specific for the reference nucleic acid sequence with or without a segment noncontiguous to a second priming sequence in the presence of a second oligonucleotide which is incapable of acting as a primer for the polymerase, wherein the second oligonucleotide has at least 5 consecutive nucleotides fully complementary to at least 5 consecutive nucleotides of the third primer; (iv) measuring the amplification of the target nucleic acid; and (v) comparing the amplification of the target nucleic acid sequence to the amplification of the reference nucleic acid sequence in the specimen.

The polymerase is generally a DNA polymerase, e.g., a thermostable polymerase.

As used herein, the "target nucleic acid sequence" is a genomic region, e.g., a portion of a gene defined by PCR primers, whose copy number is suspected of being altered, i.e., deleted or amplified. The "reference nucleic acid sequence" is a genomic region whose copy number is known, e.g., an autosomic marker such as IGF-1, or a sex chromosome marker such as the amelogenin genes AMGX and AMGY on the X and Y chromosomes, respectively. The reference nucleic acid can also be a sequence suspected or known to be amplified when the target nucleic acid corresponds to a nucleic acid sequence suspected or known to be deleted.

The biological specimen can be any biological tissue or fluid which contains, or is suspected of containing, DNA. Thus, a biological fluid includes a cell-free fluid, i.e., a fluid containing no cells or only a residual amount of cells. Examples of biological fluids can include, therefore, serum, plasma, cerebrospinal fluid, bronchial washings, a serous secretion, urine or urine sediment, sweat, tears, lavage of various tissues, saliva, tears, cerumen, pus, and stool. Among these fluids, serum, plasma, cerebrospinal fluid, serous secretions, urine, sweat, and tears are considered to be cell-free biological fluids. The biological specimen can also include nail clippings, hair, and skin.

In a preferred embodiment, four fluorophores are covalently attached to the first and third primers, and to the first and second oligonucleotides, respectively. One of the two fluorophores for the first primer and the first oligonucleotide is a donor fluorophore, and the other is an acceptor fluorophore, so that when the first primer and the first oligonucleotide are hybridized, the donor fluorophore and the acceptor fluorophore are in close proximity to allow resonance energy transfer therebetween. Similarly, one of the two fluorophores for the third primer and the second oligonucleotide is a donor fluorophore and the other is an acceptor fluorophore, so that when the third primer and the second oligonucleotide are hybridized, the donor fluorophore and the acceptor fluorophore are in close proximity to allow resonance energy transfer therebetween.

When fluorophores are attached to the primers, the detecting step is performed by monitoring the fluorescent emission change of the acceptor fluorophore upon irradiation of the donor fluorophore with an excitation light. The fluorescence decrement is directly proportional to the amount of PCR occurring, where the decrement is a function of the extent of the primer or primers being dissociated from their corresponding oligonucleotides and being incorporated into amplification products.

The amplifying steps can optionally be performed in the presence of a third oligonucleotide and a fourth oligonucleotide which are incapable of acting as primers for the polymerase, wherein the additional third oligonucleotide has at least 5 consecutive nucleotides fully complementary to at least 5 consecutive nucleotides of the second primer, and the fourth oligonucleotide has at least 5 consecutive nucleotides fully complementary to at least 5 consecutive nucleotides of the fourth primer.

In another aspect, the invention provides a kit for detecting the copy number of a target nucleic acid relative to a reference nucleic acid. The kit can include (i) a first primer with or without a segment noncontiguous to a first priming sequence, (ii) a second primer with or without a segment noncontiguous to a second priming sequence, in which the first and second primers are to be used with a polymerase for the amplification of the target nucleic acid; (iii) a third primer with or without a segment noncontiguous to a third priming sequence, (iv) a fourth primer with or without a segment noncontiguous to a fourth priming sequence, in which the third and fourth primers are to be used with a polymerase for the amplification of the reference nucleic acid, (v) a first oligonucleotide which is incapable of acting as a primer for the polymerase and has at least 5 consecutive nucleotides fully complementary to at least 5 consecutive nucleotides of the first primer; and (vi) a second oligonucleotide which is incapable of acting as a primer for the polymerase and has at least 5 consecutive nucleotides fully complementary to at least 5 consecutive nucleotides of the third primer, wherein each of the first primer, the second primer, the third primer, fourth primer, first oligonucleotide and second oligonucleotide contains 10–50 nucleotides. Preferably, the first oligonucleotide and second oligonucleotide have at least 8 consecutive nucleotides fully complementary to at least 8 consecutive nucleotides of the first primer. The kit can optionally include an additional third oligonucleotide and fourth oligonucleotide which are incapable of acting as a primer for the polymerase, wherein the third and fourth oligonucleotides contain 10–50 nucleotides, and have at least 8 consecutive nucleotides fully complementary to at least 8 consecutive nucleotides of the second primer and the fourth primer, respectively.

The methods described herein can be used in any situation in which it is desirable to determine the copy number of a target nucleic acid relative to a reference nucleic acid sequence. Thus, the method can be used to identify alterations, e.g. deletions or amplifications, of a target sequence that are indicative of the presence of cancer. The method can also be used to identify genetic disorders due to dosage anomalies, such as those occurring in Charcot-Marie Tooth Disease and Di George syndrome.

The method of determining the relative copy number can be performed rapidly, noninvasively, and is sufficiently sensitive to detect abnormal genotypes in small amounts of DNA, e.g., about 10–100 copies of a sequence to be amplified. Moreover, the technique can be applied to DNA readily obtainable biological fluids such as those described above.

A further advantage of the method is that all subjects and unique marker sequences are informative, thus eliminating the need to identify polymorphic markers in a subject. In addition, the assay efficiently detects both amplifications and deletions of a target sequence.

Other features and advantages of the present invention will be apparent from the following detailed description of the invention, and from the claims.

DETAILED DESCRIPTION

The present invention offers a direct way to measure the relative copy number of a target nucleic acid sequence and a reference nucleic acid sequence in DNA from any source (henceforth, a "test DNA sample"). The test DNA sample can be from (but is not limited to) a tissue, a tumor, bodily fluid, a preparation of any type containing cells, or DNA from lysed cells. The relative copy number of the target and reference nucleic acid sequences is preferably performed by following a quantitative decrement in fluorescence occurring after PCR ("QPCR"), which is described in U.S. Pat. Nos. 5,567,583 and 5,348,853, on the target and nucleic acid sample. In QPCR, one of the primers used for each PCR reaction is attached to an oligonucleotide duplex that carries a fluorescent molecule on each of the two strands. The fluorescent molecules are set up so that the emission frequency of the first fluorophore (e.g., fluorescein; F) on strand 1 is equal to the excitation frequency of the second fluorophore (e.g., Texas Red; T) on strand 2. F is excited by a light source whose output is at the excitation frequency of F; F then emits at a frequency which equals the excitation frequency of T. Since T is so close to F, T becomes excited by the emission of F, and then T emits. The net result is energy transfer between F and T: the complex containing the strand with F, close to the strand with T, is stimulated by the light source so that F, and then T, emits.

If PCR does occur, then the strand carrying T is displaced from the strand carrying F by the PCR-mediated elongation of the strand complementary to the F-carrying strand. In this case, energy transfer is lost as F and T are now too far apart for energy transfer to occur. As a result, stimulation of F yields an emission by F which cannot excite T, as T is too far away from F (energy transfer depends on the sixth power of the distance between F and T). No excitation of T means that T does not emit. Thus, successful occurrence of PCR yields a diminution of the fluorescent emission by T, no longer linked to F, upon stimulation by the laser. The extent of disruption (and hence the emission by T) depends directly on the amount of PCR that is generated. Thus, PCR can be quantified directly and accurately by measuring the decrement in fluorescence that results from decreased energy transfer.

Primers containing donor and acceptor fluorophores can be provided in a PCR reaction by adding a partially duplex oligonucleotide, e.g., an AMPLISENSOR™ fluorogenic signal duplex oligonucleotide (Biotronics Corp., Lowell, Mass.). The donor and acceptor fluorophores are in the duplex region of the AMPLISENSOR™ oligonucleotide, while the single-stranded region of the AMPLISENSOR™ oligonucleotide is a primer for the PCR reactions, i.e., the priming strand.

Fluorescence can be measured in a well of a 96 well microtiter dish. Since this measurement is made before a significant amount of the PCR template is generated, it is possible to determine the degree of PCR that has occurred in real time (after any given number of PCR cycles). PCR is measured in subsequent cycles by monitoring the fluorescence decrement after any cycle. Determination of the amount of PCR at any given cycle number allows PCR to be monitored in situ in the same microtiter dish in which PCR occurs. Thus, post-PCR handling does not occur. In addition, PCR is measured in real time at different time points, permitting a quantitative analysis of the PCR process.

Fluorescence can be analyzed using signal processing systems known in the art, e.g., ASAP™ software (Biotronics Corp., Lowell, Mass.); and a AG-9600 AMPLISENSOR™

Analyzer (Biotronics Corp., Lowell, Mass.). In this system, the fluorescence of each reaction is detected via a bottom reading mechanism. The signal is registered in digital format and processed according to a default algorithm, which converts the raw reading into a normalized data set for standard curve interpolation. The fluorescent-PCR assay requires both the base reading data set and the assay cycle data set for quantitation. The base reading data set represents the initial signal reading acquired prior to any detectable PCR-induced signal changes. The assay cycle data set consists of signal readings measured after any number of user-selected PCR cycles (the microtiter dish with the samples undergoing PCR is alternately placed in a thermocycler and the fluorescence plate reader, thereby allowing for alternate polymerization and reading). The readings of each data set are normalized, allowing determination of PCR by the decrease in fluorescence resulting from PCR. The well-to-well signal variation intrinsic to each data point comes mainly from factors such as geometric irregularity of the microplate wells and pipetting related inaccuracy. This signal interference can be eliminated through a normalization process using the base reading which takes into account both the background noise and the energy transfer coefficient. The detection index derived from the normalized data is equivalent to the signal departure of each sample from that of the negative standard. Thus, the value of the detection index reflects the relative amount of amplified target.

Quantitative analysis yields the amount of target sequence present in the sample based on the linear regression curve derived from a set (at least three dilutions) of positive standards. Linear regression fitting is based on the principle of least mean square analysis to correlate the quantity and detection index using the linear equation derived from the positive standard set. To optimize the fitting, the program intentionally discards those standards that deviate the most from linearity (ASAP software; Biotronics Corp., Lowell, Mass.). Since both sequences are investigated in both the test sample of bodily fluid and in a control DNA sample, the quantity of DNA from a given cell line does not factor into the final result. This obviates the need to perform precise measurement of the DNA concentrations from the cell lines to be analyzed.

To determine the relative number of the target and reference nucleic acid sequences, two PCR amplifications can be performed using the QPCR method on the test DNA sample. Preferably, sets of PCR primers are used that are able to amplify each nucleic acid sequence in a sequential asymmetric and nested PCR procedure as described in U.S. Pat. No. 5,567,583. The test and control samples are first subjected to the asymmetric PCR procedure, in which one of the primers is present in excess relative to the second primer in order to generate sufficient template strand. This strand is the strand complementary to the single-stranded region of the partially duplex AMPLISENSOR™ primer, which constitutes the third primer in the reaction.

Comparing the amount of amplification of the two DNA sequences following QPCR reveals the relative copy number of the DNA sequences in the test DNA sample. For example, the relative copy numbers of the target and reference nucleic acids can be derived by dividing the fluorescence decrement of the target nucleic acid sequence by the fluorescence decrement of the reference second nucleic acid sequence following QPCR on each sequence.

To ensure that the variation in fluorescence decrement between the two sequences is due to differences in the copy numbers of the respective sequences, and not due to differences in the ability of either of the sequences to be amplified, two PCR reactions (amplifying the two sequences) are also preferably performed on a control DNA sample, in which the relative copy number of the first marker to the second marker is known. An example of a control DNA sample is white blood cell DNA from a normal individual. QPCR is performed on the target and reference nucleic acid from the control DNA sample, and the ratio of the reaction products following QPCR for the control DNA sample are compared as above. When the ratio of target to reference nucleic acids in the test DNA sample is divided by the ratio of the target to reference nucleic acid in the control DNA sample, a final ratio is obtained which gives the desired relative copy numbers of the two nucleic acid sequences in the test DNA sample of interest. Dividing the ratios in this manner normalizes the relative efficiencies of the PCR reactions on the target and reference nucleic acids and thus removes variation in PCR amplification due to the relative amplifiability of the two loci.

Thus, in a preferred method of determining the relative copy number of the target and reference nucleic acids in the test DNA sample, a total of four QPCR reactions can be performed using two different sources of DNA. These four reactions include QPCR of target and reference nucleic acids of the test DNA sample, corresponding to the biological specimen taken from a subject, and QPCR of target and reference nucleic acids from the control DNA sample.

When the ratio is calculated by dividing the QCPR of the target nucleic acid by the QPCR of the reference nucleic acid, a ratio of 0.8–1.3 in general means that the two sequences are present in the same relative copy number. A ratio of less than 0.8 indicates the target nucleic acid sequence is present in lower copy number than the reference nucleic acid. A ratio of greater than 1.3 is indicative of an amplification of the target DNA sequence relative to the reference nucleic acid sequence.

To increase the sensitivity of the assay, the first and second DNA sequences can be selected to maximize quantitative differences between the two sequences. For example, the target nucleic acid can correspond to a sequence whose copy number is known to be or suspected of being amplified, and the reference nucleic acid can be one whose copy number is known or suspected of being deleted in the test sample.

In some applications it may be desirable to first perform QPCR using a probe specific for only the target nucleic acid sequence. One probe PCR is desirable in situations where amplification of the target nucleic sequence probe is indicative of an abnormal state due to the presence of a significant amount of nucleic acid in a sample of a bodily fluid that is normally substantially acellular. Thus, one probe PCR is desirable when very low amounts of DNA, e.g., less than about 50–100 copies of a target sequence, are expected to be present in a normal, i.e., disease free, sample. A negative PCR signal following one-probe PCR suggests the test nucleic sequence is not amplified, obviating the need to perform additional QPCR. Conversely, an abnormally high signal suggests the presence of unusually large numbers of cells, which can be either noncancerous or cancerous.

When the bodily fluid is urine sediment, for example, a high number of cells may be due to the presence of interstitial cystitis, comprising normal cells, or to the presence of cells from a bladder cancer. If the PCR result using the target nucleic acids alone suggests the presence of abnormal cells, the sample can then be further processed for QPCR using the reference nucleic acid. By performing a first QPCR specific for the target nucleic acid, resources can be conserved in not further testing samples that do not show amplification of the target nucleic acid.

QPCR detects a useful quantitative abnormality in virtually every tumor using a small number of probes. One use of this technique is therefore to determine the presence of cancer cells before, during, and after various cancer-treating regimens (e.g., surgical, radiological, chemotherapeutic protocols, or a combination of these) by measuring alterations in the ratio of the target and reference nucleic acids in a bodily fluid such as serum during the course of treatment. The combination of target and reference nucleic acids appropriate for monitoring therapy of a particular cancer in any given individual can be chosen by first determining the relative ratios of target and reference nucleic acids in DNA isolated from the tumor whose treatment is to be monitored.

In general, the DNA to be investigated can be derived from any biological specimen suspected of manifesting an alteration in copy number, e.g. (but not limited to), tumor tissues, excreted cells or body fluids. For example, because of the potential presence of tumor DNA in serum/plasma, and the preferential exfoliation of tumor cells into urine sediment, it is possible to detect differences in the DNA of these samples, if such differences are present, using QPCR.

Standard methods well known in the art can be used to isolate genomic DNA from bodily fluids, tumors, and cell lines. For example, DNA from biological fluids can be isolated using an ACUGEN™ DNA Extraction kit (Biotronics Corp., Lowell, Mass.).

Because DNAs from tumor samples and bodily fluids are usually contaminated with DNA from normal cells (whose DNA will not demonstrate copy number alterations), genome instability in cancer cells can actually be underestimated. Nevertheless, the QPCR assay is sufficiently sensitive to detect copy number changes in body fluids such as serum, plasma or urine sediment, as well as in tumors.

Without further elaboration, it is believed that one skilled in the art can, based on the description herein, utilize the present invention to its fullest extent. All publications cited herein are hereby incorporated by reference. The following specific examples are, therefore, to be construed as merely illustrative, and not limitive of the remainder of the disclosure.

EXAMPLE I

The QPCR Assay Shows Test Markers Have Eusomic Copy Numbers in Normal DNA

QPCR was performed in a 96 well plate (PTC-100, MJ Research) as described in U.S. Pat. No. 5,567,583, and directly analyzed in situ for energy transfer using a microplate fluorometer controlled by a workstation (Biotronics Corp.; Wang et al., 1995). To quantify the decrease in energy transfer, fluorescence readings from each reaction were compared to readings from a control reaction without polymerase. This control provided a reference for the maximum initial fluorescent signal, since PCR did not occur. To compensate for well-to-well variations among the PCR reactions in the plate, all data were normalized using an initial reading (base reading) taken one cycle after adding the AMPLISENSOR™ oligonucleotide detection duplex. Each reaction was repeated multiple times.

Only water was added to the blank well. For the Apex well, everything except Taq DNA polymerase was added. For the negative well, everything except genomic DNA was added.

Asymmetric PCR reactions were performed to generate sufficient template for the second (nested) PCR reaction. Use of a nested PCR system also increases the fidelity of the PCR reaction. The nested PCR reaction was initiated by adding a nested third, partially duplex, primer carrying an AMPLISENSOR™ oligonucleotide duplex (Wang et al., 1995) with fluorescein on one strand and Texas Red on the other strand. The initial asymmetric PCR was performed in 10 $\mu$l of 50 mM Tris-HCl, pH 8.7, 50 mM KCl, 5 mM $NH_4Cl$, 5 mM $MgCl_2$, 1 mM DTT, 0.1% Triton X-100, 0.2 U of Taq DNA polymerase, 90 ng of excess primer and 12 ng of limiting primer.

The genomic DNAs were present in the range of $5 \times 10^2$ to $1 \times 10^4$ copies per $\mu$l of the DNA sequence to be amplified, using 50 ng/ml of yeast tRNA as the dilution solution. An aliquot of 2.5 $\mu$l from each dilution was used for PCR. The asymmetric PCR profile for the reaction was followed dynamically by monitoring fluorescence following the addition of the AMPLISENSOR™ oligonucleotide duplex. The reaction is performed as two sequential nested PCR amplifications to increase the specificity and to enable enough sequence to accumulate in the first reaction to enable quantitative PCR following the addition of the fluorescent AMPLISENSOR™ oligonucleotide duplex.

Fluorescence signals were analyzed using ASAP™ software (Biotronics Corp., Lowell, Mass.) and a AG-9600 AMPLISENSOR™ Analyzer (Biotronics Corp., Lowell, Mass.).

Genomic DNA Isolation

Genomic DNAs were isolated using ACUGEN™ Extraction kits (Biotronics Corp., Lowell, Mass.) or QIAMP™ DNA extraction kits (QIAGEN Inc., Valencia, Calif.). DNAs were isolated from normal white blood cells, from tumor samples, from urine sediments and from serum in these examples that illustrate the potential of the technique which could be applied to any cell type or fluid from which DNA can be isolated. When isolating genomic DNAs, it was necessary to remove contaminating protein to accurately perform QPCR.

PCR Primers for Measurement of Genomic Sequence Copy Number

The copy number of D9S1752 (p16; Mao et al., Science 271:659, 1996), p53 (Lee et al., Cell 81:1013, 1995), BRCA1 (Futreal et al., Science 266:120, 1994; Miki et al., Science 266:66, 1994), erbB-2 (Slamon et al., Science 244:707,1989) cyclin D1 (Arnold, J. Invest. Med. 43:543, 1995), and UT40 (Kalikin et al., Genes Chromosome Cancer 17:64, 1996) were determined using QPCR with the following primers.

(1) BRCA1 (chromosome 17)
limiting: 5'-CCCAGAGTCAGCTCGTGTTG-3' (SEQ ID NO:1)
excess: 5'-GGGTCAGGCCAGACACCACCATGG-3' (SEQ ID NO:2)
AMPLISENSOR™ priming strand:
5'-AATTGACAGCTTCAACAGAAAGG-3' (SEQ ID NO:3)

(2) SUPT4H (chromosome 17):
limiting: 5'-AAGGTGGCAGCTGAGTGG-3' (SEQ ID NO:4)
excess: 5'-CTGAGTCTGAATTGGAGG-3' (SEQ ID NO:5)
AMPLISENSOR™ priming strand:
5'-CTGCTTATTTCTTGTTCTGG-3' (SEQ ID NO:6)

(3) erbB-2 (chromosome 17):
limiting: 5'-ACTGAAAGCCTTAGGGAAGC-3' (SEQ ID NO:7)
excess: 5'-AAGCACTCTGTACAAAGCCTGG-3' (SEQ ID NO:8)
AMPLISENSOR™ priming strand:
5'-TACTGCCCCCCATGAGGAAGGAAC-3' (SEQ ID NO:9)

(4) IGF-1 (chromosome 12):

limiting: 5'-GATGAGGCAAAGACTATGCCG-3' (SEQ ID NO:10)

excess: 5'-CCCAGGTACCCTTCTCCCAGAGTGG-3' (SEQ ID NO:11)

AMPLISENSOR™ priming strand: 5'-TACTAGGCTGCCTGTCACTGTC-3' (SEQ ID NO:12)

(5) p53 (chromosome 17)

limiting: 5'-CTTTTCACCCATCTACAGTCC-3' (SEQ ID NO:13)

excess: 5'-GGCCAGGCATTGAAGTCTCATGG-3' (SEQ ID NO:14)

AMPLISENSOR™ priming strand: 5'-TCTGTGACTTGCACGGTCAGTTGC-3' (SEQ ID NO:15)

(6) cyclin D1 (chromosome 11)

limiting: 5'-AGACCTCCAGCATCCAGGTGG-3' (SEQ ID NO:16)

AMPLISENSOR™ priming strand: 5'-GCATCGGGGTAZGCGCGGCGGATGG-3' (SEQ ID NO:17)

excess: 5'-CCACTCCTGTGCTGCGAAGTGG-3' (SEQ ID NO:18)

(7) D9S1752 limiting: 5'-TCTGATGTGTCCTACTCCAC-3' (SEQ ID NO:19)

excess: 5'-GCAAGTCATAAGGGGATTTC-3' (SEQ ID NO:20)

AMPLISENSOR™ priming strand: 5'-GTTACAATTGCTCTCACTCCACTCC-3' (SEQ ID NO:21)

(8) UT40 limiting: 5'-AGCTGGGGAATAGAGTGAGATTC-3' (SEQ ID NO:22)

excess: 5'-AAATTGCATGTCTCTGGGGTACGGA-3' (SEQ ID NO:23)

AMPLISENSOR™ priming strand:

5'-AGAAAGAAAGATAGACAGACAAACG-3' (SEQ ID NO:24)

For the experiments shown in Table 1, QPCR was performed using primers specific for the indicated genes or loci as target nucleic acids in normal human DNA. The copy number of these nucleic acids was then compared to determine the copy number of the reference marker IGF-1 following QPCR. Markers examined included p53, BRCA1, cyclin D1, and erbB-2, and the marker D9S1752, which is located 10 kb from the p16 gene.

As is demonstrated in Table 1, the ratio of the indicated target nucleic acids to the reference IGF-1 nucleic acid ranged from 0.8–1.3. Because p53, BRCA1, D9S1752, erbB-2, cyclin D1 and IGF-1 are all found on autosomes, all the sequences will occur in approximately the same copy number in normal DNA. Thus, the data in Table 1 establish the reproducibility of the QPCR procedure and document the invariance of copy number in genomic DNA derived from a normal source. They also establish the normal variability of the assay, and in subsequent experiments values from 0.8–1.3 were not classified as abnormal.

TABLE 1

QPCR Ratios of Selected Target Nucleic Acids to Reference Nucleic Acid IGF-1 in DNA from White Blood Cells of Normal Individuals

| SAMPLE | p53 | BRCA1 | D9S1752 | erbB-2 | cyclin D1 |
|---|---|---|---|---|---|
| 1 | 0.8 | 1 | 0.9 | 1.1 | 1 |
| 2 | 1.3 | 0.9 | 1.1 | 1.2 | 1.1 |
| 3 | 0.9 | 1 | 1.2 | 1 | 1.1 |
| 4 | 1 | 1.1 | 0.9 | 0.8 | 0.9 |
| 5 | 0.9 | ND | ND | 1.1 | 1.2 |
| 6 | 0.9 | 1.1 | 0.8 | ND | ND |
| 7 | 0.8 | 0.8 | 0.8 | 1.1 | 1.2 |
| 8 | 0.8 | 0.9 | 0.9 | 0.9 | 1 |
| 9 | 1 | 0.9 | ND | 0.9 | 1 |
| 10 | 1 | 0.9 | 0.8 | 1.2 | 1.1 |
| Average | 0.94 | 0.96 | 0.93 | 1.03 | 1.07 |
| Std. Dev. | 0.15 | 0.15 | 0.15 | 0.14 | 0.1 |
| QPCR Range | 0.8–1.3 | 0.8–1.3 | 0.8–1.2 | 0.8–1.2 | 0.9–1.2 |

ND = Not Determined

EXAMPLE II

Relative QPCR Reveals DNA Sequence Copy Number Alterations in DNA From Cancer Tissues The relative copy numbers of tumor suppressor markers (p53, D9S1752 (p16), or BRCA1) and/or an oncogene (erbB-2 or cyclin D1) were determined using the conditions described in Example I using QPCR in DNA isolated from esophageal, breast, prostate, colon, cervical, adrenal, bladder, brain, kidney, larynx, pancreas, and neuroblastoma tumors. The marker UT40 was also used to mark the distal part of the long arm of chromosome 17 in some experiments.

The results using DNA from breast, prostate and colon tumors are shown in Table 2. The tumor suppressor loci p53 and BRCA1 were present in lower copy numbers relative to the reference marker (IGF-1) in the breast tumor tissues. The lowered copy number was not simply due to aneusomy for chromosome 17 because the quantities of p53, BRCA1 and UT40, all of which reside on chromosome 17, were often discordant in a given sample. Amplifications of these loci relative to IGF-1 are more rare in breast cancer than in other malignancies investigated, but amplifications of these tumor suppressor markers have been observed in samples from other breast cancers.

Table 2 also demonstrates variations in the copy number of p53 and BRCA1 relative to IGF-1 in DNA isolated from prostate cancer tissues. In the examples shown, p53 sequences were found to be amplified, while both amplifications and deletions of BRCA1 relative to IGF-1 were detected. The lack of correspondence between the types of quantitative alterations observed for these two tumor suppressor markers on chromosome 17 is further evidence that the quantitative alterations reflect amplification or deletion involving specific regions of the chromosome rather than resulting from simple aneusomy of an entire chromosome.

TABLE 2

QPCR Ratios of Selected Target Nucleic Acids to
Reference Nucleic Acid IGF-1 in
DNA from Tumor Cells (ND = Not Determined)

BREAST TUMORS

| Marker and chromosomal location Sample | p53 17p13 | BRCA1 17q11.2 | cyclin D1 11q13 | UT40 17q25 |
|---|---|---|---|---|
| 1 | 0.8 | 0.6 | 0.5 | 1.1 |
| 2 | 0.6 | 0.5 | 0.2 | 1.1 |
| 3 | 0.7 | 0.9 | 1.5 | 0.9 |
| 4 | 0.7 | 0.7 | 0.7 | 1.3 |
| 5 | 0.4 | 1.2 | 0.4 | 1.7 |

PROSTATE TUMORS

| Marker and chromosomal location Sample | LOH Analysis for p53 | p53 17p13 | BRCA1 17q11.2 | UT40 17q25 |
|---|---|---|---|---|
| 6 | Uninformative | 1.3 | 1.4 | 1 |
| 7 | Uninformative | 1.8 | 0.4 | 1.1 |
| 8 | No LOH | 2.6 | 1 | 0.8 |
| 9 | No LOH | 2.1 | 0.6 | ND |
| 10 | No LOH | 1.6 | 4.2 | 1.2 |
| 11 | No LOH | 4 | 4 | 1.1 |
| 12 | No LOH | 7.2 | 0.1 | ND |
| 13 | No LOH | 5.7 | 0.2 | 0.6 |

COLON TUMORS

| SAMPLE | LOH Analysis | p53 17p13 | 17q11.2 BRCA1 | UT40 17q25 |
|---|---|---|---|---|
| 14 | ND | 1.3 | 3.7 | 1 |
| 15 | ND | 0.9 | 0.8 | 1.2 |
| 16 | No LOH | 2.3 | 0.9 | 1 |
| 17 | No LOH | 1.9 | 2 | 0.9 |
| 18 | Uninformative | 2.1 | ND | 1 |

Table 2 also shows the results of QPCR using DNA isolated from colon cancer tissues using p53 and BRCA1 as the target probes. p53 sequences were amplified in three of five samples, while BRCA1 was amplified in two of four samples examined. However, amplification of the p53 locus did not correlate with amplification of BRCA1. In addition, UT40 (a marker at 17q25) was usually present at normal copy number, suggesting again that amplification of larger regions of chromosome 17 was not responsible for the alterations in sequence copy number seen in the colon cancer tumors.

Loss of heterozygosity (LOH) was also monitored in some of the prostate and colon samples subjected to QPCR analysis. LOH was not observed in several samples although anomalies (e.g., relative amplifications of p53 relative to IGF-1) were observed. This also illustrates that amplification can occur in the absence of LOH, underscoring that relative amplification of tumor suppressor genes can occur earlier than LOH. Thus, QPCR is a more sensitive indicator than LOH of the genome instability that occurs in cancer cells but not in normal cells.

QPCR was also used to examine sequence copy number in bladder tumors. In these experiments, the copy number of the D9S1752 locus was examined relative to the copy number of IGF-1 in DNA from 70 primary bladder tumors. The D9S1752 locus is located is located 10 kb from the tumor suppressor gene, p16, which is frequently deleted in bladder tumors (Cairns et al., Nature Genetics 11,210, 1995). In these experiments, QPCR results were also compared to conventional PCR-based microsatellite analysis, which detects differences in sizes of small repeat units in the genome (see Lasko et al., Ann. Rev. Genet. 25,:281, (1991). In addition, some tumors were monitored for LOH.

Of the 70 tumors, eleven were not informative by microsatellite analysis. Of the remaining tumors, 39 of 59 (66%) demonstrated a deletion at D9S1752 by conventional microsatellite analysis. Of these 39, 22 were homozygous deletion (HD) cases and 19 were LOH. In 53 of the 59 informative tumors, there was concordance between results obtained using QPCR and microsatellite analysis. In particular, the two techniques agreed on all 39 samples in which standard polymorphism analysis showed either HD or LOH. In 14 samples, both QPCR analysis for D9S1752/IGF-1 and microsatellite analysis for D9S1752 indicated that the samples were normal.

Seventeen samples were normal or uninformative by microsatellite analysis but were scored as abnormal by QPCR. Of these 17 samples, eleven tumors were not polymorphic at D9S1752 and could not be evaluated by LOH analysis. However, because QPCR does not require polymorphism, it could be used to evaluate these 11 tumors. In all these cases, the QPCR analysis was informative and revealed an abnormal copy number of D9S1752 relative to IGF-1. Ten samples showed deletion of D9S1752, while one had an amplification of D9S1752.

Three of the 17 samples informative by QPCR but not by microsatellite analysis showed amplification of D9S1752. Further, QPCR revealed a decrease of the D9S1752/IGF-1 ratio sequences when microsatellite analysis showed 2 alleles for this locus in four samples. Use of another autosomal probe, D21S100β, showed that the IGF-1 locus was amplified in these samples.

Overall, QPCR was sufficiently sensitive to detect all abnormalities detected by microsatellite analysis. In addition, QPCR detected both decreases and increases in the D9S1752/IGF-1 ratio in samples for which microsatellite analysis of D9S1752 was not informative.

EXAMPLE III

Relative QPCR Reveals Specific DNA Sequence Copy Number Alterations in Nucleic Acids Isolated From Bodily Fluids of Patients With Tumors.

Urine sediment can be used to monitor the presence of bladder tumor cells because cells from bladder tumors are often exfoliated into urine sediment. Accordingly, QPCR was performed on DNA isolated from urine sediment in order to determine the relative copy number of the D9S1752 locus to IGF-1 using the conditions described in Example I.

Table 3 shows the copy number of D9S1752 relative to IGF-1 in urine sediment from eight individuals diagnosed with bladder cancer. All of the individuals had an abnormal D9S1752/IGF-1 ratio, with seven showing deletions of D9S1752 and one showing amplification.

For some of the subjects, the D9S1752/IGF-1 ratio was also determined in DNA taken from the bladder tumor or from plasma. The bladder tumor samples were obtained from patients whose urine sediment results were informative. The bladder tumor samples similarly showed a decreased copy number of D9S1752 relative to IGF-1. LOH studies were also performed on some of the subjects shown in Table 3 and yielded results consistent with the results obtained in DNA from urine sediment: three samples showing LOH or HD also had a reduced copy number of D9S1752. One sample, which had an amplified D9S1752/

IGF-1 ratio of 1.5, was normal by LOH analysis. For all the blood samples shown in Table 3, the D9S1752/IGF-1 ratio was in the normal range as expected. These results demonstrate that relative QPCR performed on DNA isolated from urine sediment can measure sequence alterations indicative of bladder cancer.

TABLE 3

QPCR in DNA from Urine Sediment, Bladder Tumors, and Serum
(ND = Not Determined)

| Probe Samples | D9S1752/IGF-1 Bladder tumor | D9S1752/IGF-1 Urine sediment | LOH studies of D9S1752 | D9S1752/IGF-1 Blood samples |
|---|---|---|---|---|
| 1 | ND | 0.2 | LOH | ND |
| 2 | ND | 0.2 | HD | ND |
| 3 | ND | 1.5 | NO LOH | ND |
| 4 | ND | 0.6 | HD | 1 |
| 5 | 0.3 | 0.2 | ND | 0.8 |
| 6 | 0.1 | 0.4 | ND | 1 |
| 7 | ND | 0.1 | HD | 1 |
| 8 | 0.2 | 0.4 | ND | 1 |

Relative QPCR was also used to examine sequence alterations in DNA from bodily fluids of patients suffering from bladder, breast, lung, nasopharyngeal, esophageal, or prostate cancer. Shown in Table 4 are the erbB-2/IGF-1 or D9S1752/cyclin D1 ratios following QPCR on DNA isolated from the serum of prostate cancer patients, as well as DNA isolated from some of the corresponding prostate tumors. Eight of ten samples isolated from serum DNA showed abnormal erbB-2/IGF-1 ratios, which ranged from 1.7 to 4.5 in the samples tested. In DNA isolated from the tumors of the two patients with normal serum erbB-2/IGF-1 ratios, the corresponding erbB-2/IGF-1 ratio was abnormal.

Sequence abnormalities were also measured by following the D9S1752/cyclin D1 ratio following QPCR in DNA isolated from the serum of an additional five prostate cancer patients. Four of the five patients showed an elevation in the D9S1752/cyclin D1 ratio. For the tumor showing normal D9S1752/cyclin D1 serum levels, DNA from the corresponding tumor showed an altered ratio.

TABLE 4

Comparison of Various QPCR Ratios in DNA from Serum and Tumor Samples of Prostate Cancer Patients
(ND = Not Determined)

| SAMPLE | SERUM DNA erbB-2/IGF1 | TUMOR DNA erbB-2/IGF1 |
|---|---|---|
| 1 | 4.5 | ND |
| 2 | 3.2 | 1.5 |
| 3 | 4.5 | ND |
| 4 | 3.3 | ND |
| 5 | 3.5 | ND |
| 6 | 4.2 | ND |
| 7 | 3.9 | 2.5 |
| 8 | 0.9 | 3 |
| 9 | 1.7 | ND |
| 10 | 1.1 | 2 |

| SAMPLE | SERUM D9S1752/cyclin D1 | TUMOR D9S1752/cyclin D1 |
|---|---|---|
| 11 | 1.8 | 6.7 |
| 12 | 2 | 3 |
| 13 | 4 | 4.3 |
| 14 | 2 | 5.7 |
| 15 | 1.2 | 6.2 |
| NORMAL SERUM | 1.2 | ND |
| NORMAL SERUM | 1.1 | ND |
| NORMAL WBC | 1.1 | ND |

The data demonstrate that DNA isolated from serum may have a normal ratio, which corresponds to a low tumor burden, or an altered ratio, corresponding to a high tumor burden, when the QPCR ratio in DNA isolated from the tumor itself is abnormal.

Serum was also measured for five of the patients listed in Table 4 that initially had abnormal erbB-2/IGF-1 or D9S1752/cyclin D1 ratios at six months following therapy. For four of the patients, the D9S1752/cyclin D1 ratios were in the normal range, the exceptional patient had a ratio of 1.6. Thus, QPCR can be used on bodily fluids such as serum to screen for aggressive cancer that has seeded the bloodstream prior to, during and after therapy.

QPCR was also performed using probes specific for the erbB-2 and IGF-1 loci on DNA isolated from serum of patients with breast cancer, lung cancer, nasopharyngeal cancer or esophageal cancer. Six of ten samples from sera of patients with lung cancer showed abnormal QPCR ratios, while abnormal ratios were detected in 11 of 13 samples from nasopharyngeal cancers, and in 13 of 20 samples from sera of esophageal cancers.

EXAMPLE IV

QPCR Using One Probe Distinguishes Cell-free and Cell-containing Samples in DNA Isolated From Urine Sediment.

To detect the presence of DNA, which is indicative of the presence of cells, in urine sediment, QPCR was performed on DNA isolated from urine sediment using primers specific for the erbB-2 gene. Although this assay does not distinguish between normal and abnormal cell types, it provides a rapid and quantitative indication that cells are present in a fluid that is normally cell-free.

QPCR using a probe for the erbB-2 locus was performed on DNA isolated from urine sediment in healthy individuals, individuals with non-malignant bladder conditions such as cystitis and urinary tract infections, and individuals with bladder cancer. The amount of DNA present in urine sediment was then compared to the underlying bladder condition, if present. The data obtained from urine sediment could be grouped into three classes, according to how much DNA was isolated: (a) low amounts of DNA (less than about 50–100 copies of a target DNA sequence in cells sedimented from 50 $\mu$l of urine), which was seen only in normals without significant number of cells in the urine; (b) medium amounts of DNA (about 50–100 copies of the target DNA sequence in cells sedimented from 50 $\mu$l of urine), which were seen with either condition; and (c) high amounts of DNA (more than about 50–100 copies of the target DNA sequence in cells sedimented from 50 $\mu$l of urine), which were only seen in individuals with increased numbers of cells, either benign or malignant, in the urine. The samples were also stained with the dye Hoechst 33258; however, staining with this dye did not correlate with the presence of a bladder condition. This result demonstrates that Hoechst 33258 staining of urine sediment was not accurate in identifying abnormalities in these conditions, which examined only a small number of cells.

These results demonstrate that one-probe QPCR can be used to screen urine sediment for abnormalities such as cystitis, urinary tract infections, or bladder cancer. Thus, the one-probe PCR assay can be used to screen groups at risk for bladder abnormalities. Further, in the case of individuals with previous malignancies, low or high values of one-probe QPCR can be used as an efficacious way to evaluate the success of therapy and the need for further QPCR analysis using the second reference probe. Successful therapy is associated a low one-probe QPCR value. Failure of therapy is associated with a high QPCR reading, reflecting continued presence of the malignancy with or without an associated urinary tract infection. These two explanations can be distinguished in subsequent two-probe QPCR using a reference nucleic acid.

OTHER EMBODIMENTS

From the above description, the essential characteristics of the present invention can be ascertained. Without departing from the spirit and scope thereof, various changes and modifications of the invention can be made to adapt it to various usages and conditions. Thus, other embodiments are also within the claims.

We claim:

1. A method for determining the number of copies of a target nucleic acid relative to the number of copies of a reference nucleic acid in a biological specimen, which method comprises the steps of:
   (a) amplifying the target nucleic acid in said specimen with a polymerase, a first primer specific for said target nucleic acid with or without a segment noncontiguous to a first priming sequence, a second primer specific for said target nucleic acid with or without a segment noncontiguous to a second priming sequence in the presence of a first oligonucleotide which is incapable of acting as a primer for said polymerase, wherein said first oligonucleotide has at least 5 consecutive nucleotides fully complementary to at least 5 consecutive nucleotides of said first primer;
   (b) measuring the amplification of the target nucleic acid;
   (c) amplifying the reference nucleic acid in said specimen with a polymerase, a third primer specific for said reference nucleic acid with or without a segment noncontiguous to a third priming sequence, and a fourth primer specific for said reference nucleic acid sequence with or without a segment noncontiguous to a fourth priming sequence in the presence of a second oligonucleotide which is incapable of acting as a primer for said polymerase, wherein said second oligonucleotide has at least 5 consecutive nucleotides fully complementary to at least 5 consecutive nucleotides of said third primer;
   (d) measuring the amplification of the reference nucleic acid; and
   (e) comparing the amplification of said target nucleic acid sequence to the amplification of said reference nucleic acid sequence in said specimen to determine the number of copies of the target nucleic acid relative to the number of copies of the reference nucleic acid.

2. The method of claim 1, wherein said biological specimen is a cell-free fluid selected from the group consisting of serum, plasma, cerebrospinal fluid, a serous secretion, urine, sweat, and tears.

3. The method of claim 2, wherein said fluid is serum.

4. The method of claim 1, wherein said biological specimen is urine sediment.

5. The method of claim 1, wherein four fluorophores are covalently attached to said first primer, said third primer, said first oligonucleotide, and said second oligonucleotide, respectively, with one of said four fluorophores for said first primer and said first oligonucleotide being a donor fluorophore and the other being an acceptor fluorophore, and with one of said two fluorophores for said third primer and said second oligonucleotide being a donor fluorophore and the other being an acceptor fluorophore, so that when said first primer and said first oligonucleotide are hybridized, said donor fluorophore and said acceptor fluorophore are in close proximity to allow resonance energy transfer therebetween, and when said third primer and said second oligonucleotide are hybridized, said donor fluorophore and said acceptor fluorophore are in close proximity to allow resonance energy transfer therebetween; and, further, said measuring steps are performed by monitoring fluorescent emission change of said acceptor fluorophore upon irradiation of said donor fluorophore with an excitation light, said change being a function of the extent of said first primer being dissociated from said first oligonucleotide and being incorporated into said amplificaton product of the target nucleic acid.

6. The method of claim 5, wherein said biological specimen is a cell-free fluid selected from the group consisting of serum, plasma, cerebrospinal fluid, a serous secretion, urine, sweat, and tears.

7. The method of claim 6, wherein said fluid is serum.

8. The method of claim 5, wherein said biological specimen is urine sediment.

9. The method of claim 1, wherein said first primer and said third primer include segments noncontiguous to said first priming sequence and said third priming sequences, respectively.

10. The method of claim 9, wherein said biological specimen is a cell-free fluid selected from the group consisting of serum, plasma, cerebrospinal fluid, a serous secretion, urine, sweat, and tears.

11. The method of claim 10, wherein said fluid is serum.

12. The method of claim 9, wherein said biological specimen is urine sediment.

13. The method of claim 9, wherein said first oligonucleotide and said second oligonucleotide have at least 5 consecutive nucleotides fully complementary to at least 5 consecutive nucleotides in said noncontiguous segment of said first primer and said third primer, respectively.

14. The method of claim 13, wherein said biological specimen is a cell-free fluid selected from the group consisting of serum, plasma, cerebrospinal fluid, a serous secretion, urine, sweat, and tears.

15. The method of claim 14, wherein said fluid is serum.

16. The method of claim 13, wherein said biological specimen is urine sediment.

17. The method of claim 1, wherein said amplifying steps are performed in the presence of an additional third oligonucleotide and fourth oligonucleotide which are incapable of acting as primers for said polymerase, wherein said additional third oligonucleotide has at least 5 consecutive nucleotides fully complementary to at least 5 consecutive nucleotides of said second primer, and said additional fourth oligonucleotide has at least 5 consecutive nucleotides fully complementary to at least 5 consecutive nucleotides of said fourth primer.

18. The method of claim 17, wherein said biological specimen is a cell-free fluid selected from the group consisting of serum, plasma, cerebrospinal fluid, a serous secretion, urine, sweat, and tears.

19. The method of claim 18, wherein said fluid is serum.

20. The method of claim 17, wherein said biological specimen is urine sediment.

21. A kit for detecting the copy number of a target nucleic acid relative to a reference nucleic acid, said kit comprising:

a first primer with or without a segment noncontiguous to a first priming sequence, a second primer with or without a segment noncontiguous to a second priming sequence, which said first and second primers are to be used with a polymerase for the amplification of the target nucleic acid;

a third primer with or without a segment noncontiguous to a third priming sequence, a fourth primer with or without a segment noncontiguous to a fourth priming sequence, which said third and fourth primers are to be used with a polymerase for the amplification of the reference nucleic acid;

a first oligonucleotide which is incapable of acting as a primer for said polymerase and has at least 5 consecutive nucleotides fully complementary to at least 5 consecutive nucleotides of said first primer; and a second oligonucleotide which is incapable of acting as a primer for said polymerase and has at least 5 consecutive nucleotides fully complementary to at least 5 consecutive nucleotides of said third primer, wherein each of said first primer, said second primer, said third primer, said fourth primer, said first oligonucleotide, and said second oligonucleotide contains 10–50 nucleotides.

22. The kit of claim 21, wherein said first oligonucleotide and said second oligonucleotide have at least 8 consecutive nucleoteotides fully complementary to at least 8 consecutive nucleotides of said first primer.

23. The kit of claim 21, further comprising an additional third oligonucleotide and fourth oligonucleotide which are incapable of acting as a primer for said polymerase, contain 10–50 nucleotides, and have at least 8 consecutive nucleotides fully complementary to at least 8 consecutive nucleotides of said second primer and said fourth primer, respectively.

* * * * *